United States Patent
Motai

(10) Patent No.: US 12,048,471 B2
(45) Date of Patent: Jul. 30, 2024

(54) SEPTUM RESECTION METHOD AND ENDOSCOPIC TREATMENT DEVICE

(71) Applicant: OLYMPUS CORPORATION, Hachioji (JP)

(72) Inventor: Kosuke Motai, Hidaka (JP)

(73) Assignee: OLYMPUS CORPORATION, Tokyo (JP)

( * ) Notice: Subject to any disclaimer, the term of this patent is extended or adjusted under 35 U.S.C. 154(b) by 1024 days.

(21) Appl. No.: 16/990,502

(22) Filed: Aug. 11, 2020

(65) Prior Publication Data

US 2020/0367958 A1 Nov. 26, 2020

Related U.S. Application Data

(63) Continuation of application No. PCT/JP2018/004839, filed on Feb. 13, 2018.

(51) Int. Cl.
A61B 18/14 (2006.01)
A61B 18/00 (2006.01)

(52) U.S. Cl.
CPC .... *A61B 18/14* (2013.01); *A61B 2018/00083* (2013.01); *A61B 2018/00494* (2013.01);
(Continued)

(58) Field of Classification Search
CPC .......... A61B 18/14; A61B 2018/00083; A61B 2018/00494; A61B 2018/00601; A61B 2018/00982; A61B 2018/144; A61B 2018/1467; A61B 17/320016; A61B 17/32; A61B 17/3205; A61B 2017/320064; A61B 2017/320074; A61B 2017/320075;
(Continued)

(56) References Cited

U.S. PATENT DOCUMENTS

| 5,078,716 A | 1/1992 | Doll |
| 2012/0172864 A1 | 7/2012 | Farin et al. |
| 2013/0197515 A1* | 8/2013 | Raybin ............... A61B 18/1492 606/46 |

FOREIGN PATENT DOCUMENTS

| JP | 2008-302216 A | 12/2008 |
| JP | 2014-502184 A | 1/2014 |
| WO | 2012/066276 A2 | 5/2012 |

OTHER PUBLICATIONS

May 15, 2018 International Search Report issued in Application No. PCT/JP2018/004839.

* cited by examiner

*Primary Examiner* — Katherine M Shi
*Assistant Examiner* — Mohammed S Adam
(74) *Attorney, Agent, or Firm* — Oliff PLC

(57) ABSTRACT

An endoscopic treatment device has a sheath extending between a distal end portion and a proximal end portion; a first/second wire inserted through the sheath, wherein the first/second wire can protrude from the distal end portion of the sheath and cut tissue by being applied with current; an insulative member configured to connect distal ends of the first wire and the second wire; and a first/second insulative tube configured to cover the first/second wire protruding from the sheath, wherein the first/second insulative tube can move with respect to the first/second wire respectively, wherein the endoscopic treatment device switches between a first state where the second wire protruding from the sheath is covered by the second insulative tube and a second state where the first wire protruding from the sheath is covered by the first insulative tube.

7 Claims, 12 Drawing Sheets

(52) U.S. Cl.
CPC ............ *A61B 2018/00601* (2013.01); *A61B 2018/00982* (2013.01); *A61B 2018/144* (2013.01); *A61B 2018/1467* (2013.01)

(58) Field of Classification Search
CPC .......... A61B 2017/320077; A61B 2017/3225; A61B 18/1402; A61B 18/1492
See application file for complete search history.

SEPTUM RESECTION METHOD AND ENDOSCOPIC TREATMENT DEVICE

This application is a continuation application of a PCT International Application No. PCT/JP2018/004839, filed on Feb. 13, 2018. The contents of the PCT International Application are incorporated herein by reference.

BACKGROUND

Regarding the esophageal diverticulum including the Zenker diverticulum, the ingesta entering the diverticulum may stay in the diverticulum to cause inflammation thereto. In the situation where the hanging down esophageal diverticulum wall agglutinates with part of the gastrointestinal tract wall, it is possible to incise the agglutinated diverticulum part while observing the agglutinated diverticulum part using a flexible endoscope so as to facilitate the discharge of the contents therein from the esophageal diverticulum. It is not necessary to incise the cervix from outside by using the endoscope such that patient burden can be reduced.

A medical device used for incising the diverticulum part is generally a high-frequency knife as disclosed in Japanese Unexamined Patent Application, First Publication No. 2008-302216. IN the situation of using the high-frequency knife, the diverticulum part is cut in a linear manner by the high-frequency knife protruding from a distal end of the endoscope.

However, as time passes, the part which is cut in the linear manner may agglutinate due to the biological repairing effect. It is necessary to perform treatment again since it becomes easy for the ingesta to be accumulated in the diverticulum again. In order to prevent the agglutination, it is considered to perform the resection to the diverticulum part in a wider region rather than the incision in the linear manner; however, it is difficult to realize such resection using the endoscope and the conventional high-frequency knife.

SUMMARY

Exemplary embodiments relate to a septum resection method, more specifically, a method for partially resecting part of the septum of the gastrointestinal tract and an endoscopic treatment device configured to be suitably used in the septum resection method. According to an exemplary embodiment, an endoscopic treatment device, has a sheath having a distal end portion and a proximal end portion, the sheath extending between the distal end portion and the proximal end portion; a first wire inserted through the sheath, wherein the first wire can protrude from the distal end portion of the sheath and the first wire can cut tissue by being applied with current; a second wire inserted through the sheath, wherein the second wire can protrude from the distal end portion of the sheath and the second wire can cut tissue by being applied with current; an insulative member configured to connect distal ends of the first wire and the second wire; a first insulative tube configured to cover the first wire protruding from the sheath, wherein the first insulative tube is relatively movable with respect to the first wire and the first wire is inserted through the first insulative tube; and a second insulative tube configured to cover the second wire protruding from the sheath, wherein the second insulative tube is relatively movable with respect to the second wire and the second wire is inserted through the second insulative tube. The endoscopic treatment device is configured to be switchable between a first state in which the second wire protruding from the sheath is covered by the second insulative tube and a second state in which the first wire protruding from the sheath is covered by the first insulative tube.

According to another exemplary embodiment, part of the first wire may displace outwardly in a diameter direction of the sheath when the first wire protrudes from the sheath, and part of the second wire may displace outwardly in the diameter direction of the sheath toward an opposite direction in which the first wire displaces when the second wire protrudes from the sheath.

Additionally, the sheath may have two lumens extending from the distal end portion toward the proximal end portion of the sheath, the first wire may be inserted through one of the two lumens while being inserted through the first insulative tube, and the second wire may be inserted through the other lumen different from the lumen being inserted by the first wire while the second wire is inserted through the second insulative tube.

Additionally, the endoscopic device may include a third wire protruding from the distal end portion of the sheath toward a space between the first wire and the second wire in a lateral view made from a direction orthogonal to a plane including part of the first wire and part of the second wire protruding from the sheath, wherein the third wire can cut tissue by being supplied with current, and a third insulative tube being relatively movable with respect to the third wire, wherein the third wire is inserted through the third insulative tube and the third insulative tube covers the third wire protruding from the sheath, wherein the insulative member may be connected to a distal end of the first wire, a distal end of the second wire, and a distal end of the third wire, and the endoscopic treatment device may be switchable among the first state, the second state, and a third state in which the third wire protruding from the sheath is covered by the third insulative tube.

The third wire may also be configured to be relatively movable with respect to the first wire and the second wire.

A septum resection method for resecting part of the septum in the gastrointestinal organ can include a first groove formation process of forming a first groove penetrating the septum in a width direction; a second groove formation process of forming a second groove penetrating the septum in the width direction and substantially parallel to the first groove after the first groove formation process; a third groove formation process of forming a third groove penetrating the septum in the width direction by cutting the septum to connect the first groove and the second groove after the second groove formation process; and a dissection process of cutting off part of the septum which is surrounded by the first groove, the second groove, and the third groove from the gastrointestinal organ.

The septum resection method may also be performed using the endoscopic treatment device, and the first groove formation process may include a procedure of forming an opening end by cutting an edge portion of the septum using the first wire, the first groove may be formed to extend from the opening end, and the second groove formation process may include a procedure of forming the second groove by using the second wire while moving the first wire being insulatively covered by the first insulative tube along the first groove after cutting the edge portion of the septum by the second wire.

The septum resection method may further include a second groove formation preparation process of moving the first wire to the opening end, between the first groove formation method and the second groove formation method.

A septum resection method for resecting part of the septum in the gastrointestinal organ by using the endoscopic treatment device can include a first groove formation process of forming a first groove penetrating the septum in a width direction using a wire among the first wire, the second wire, and the third wire; a second groove formation process of forming a pair of second grooves penetrating the septum in the width direction and substantially parallel to the first groove after the first groove formation process; a third groove formation process of forming a third groove by cutting the septum and penetrating the septum in the width direction so as to connect the first groove and the second groove; and a dissection process of cutting off part of the septum which is surrounded by the first groove, the second groove, and the third groove from the gastrointestinal organ.

The first groove formation process may include a procedure of forming an opening end by cutting an edge portion of the septum using one of the first wire, the second wire, and the third wire, the first groove may be formed to extend from the opening end, and the second groove formation process may include a procedure of forming one of the pair of second grooves by using the first wire and forming the other of the pair of second grooves by using the second wire while moving the third wire being insulatively covered by the third insulative tube along the first groove after cutting the edge portion of the septum by the first wire and the second wire.

A second groove formation preparation process can include moving the third wire to the opening end, between the first groove formation method and the second groove formation method.

DETAILED DESCRIPTION OF EMBODIMENTS

An exemplary embodiment of the present invention will be described referring to enclosed FIG. 1 to FIG. 15.

Figure 1:
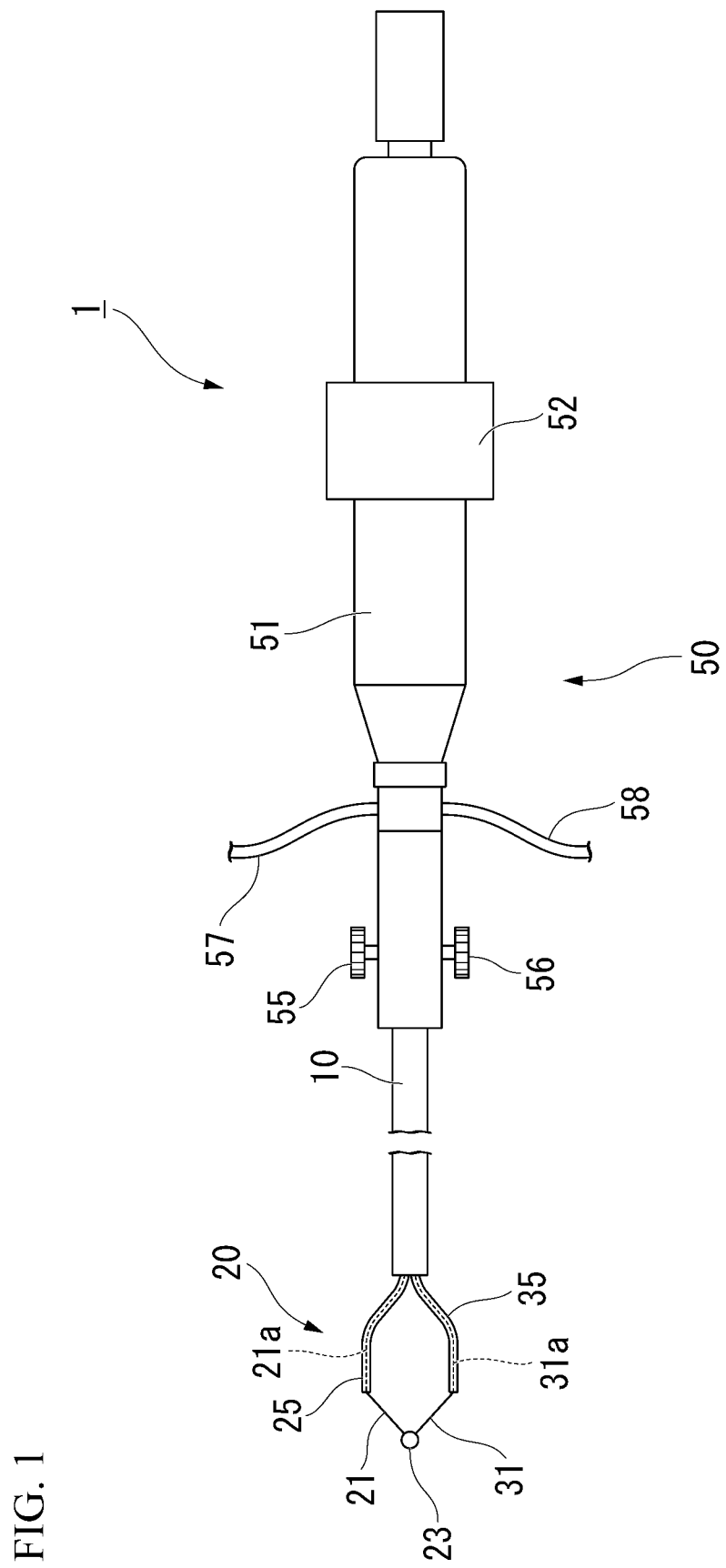
FIG. 1 is an overall view showing an endoscopic treatment device according to an exemplary embodiment.

FIG. 1 is a view showing an overall configuration of an endoscopic treatment device (hereinafter referred as a "treatment device") according to the present embodiment. The treatment device 1 has an elongated sheath 10, a cutting portion 20 inserted through the sheath 10, and an operation portion 50 connected to a proximal end of the sheath 10.

The sheath 10 is a tubular member having the electric insulation at least on an outer surface, and two independent lumens are provided therein to extend from a distal end portion to a proximal end portion. A conventional multi-lumen tube formed from resin can be used as the sheath 10.

The cutting portion 20 has a first wire 21 and a second wire 31 having electric conductivity, a first insulative tube 25 through which the first wire 21 is inserted, and a second insulative tube 35 through which the second wire 31 is inserted.

The first wire 21 and the second wire 31 are formed from a conductor such as the stainless steel, the nickel titanium alloy and the like. The first wire 21 and the second wire 31 are processed to reform the shapes thereof. When the first wire 21 and the second wire 31 are protruded from the sheath 10, part of the first wire 21 and the second wire 31 displaces outwardly with respect to a dimeter direction of the sheath 10 due to the reformation. At this time, the second wire 31 displaces outwardly with respect to the diameter direction of the sheath 10 and toward the opposite side of that of the first wire 21 so as to be apart from the first wire 21. In the state in which the first wire 21 and the second wire 31 protrude from the sheath 10, a parallel portion 21a of the first wire 21 and a parallel portion 31a of the second wire 31 which displace outwardly with respect to the diameter direction of the sheath 10 are substantially parallel with each other as shown in FIG. 1, and an interval between the parallel portion 21a and the parallel portion 31a is wider than the diameter of the sheath 10.

A distal end of the first wire 21 and a distal end of the second wire 31 are connected via an electric insulative tip (insulation member) 23. Due to the tip 23, the distal end of the cutting portion 20 has the electric insulation. Due to the tip 23, either of the parallel portion 21a and the parallel portion 31a maintains the relationship with the other.

The first wire 21 and the second wire 31, and the first insulative tube 25 and the second insulative tube 35 are configured to extend through the sheath 20 until the operation portion 50.

Figure 2:
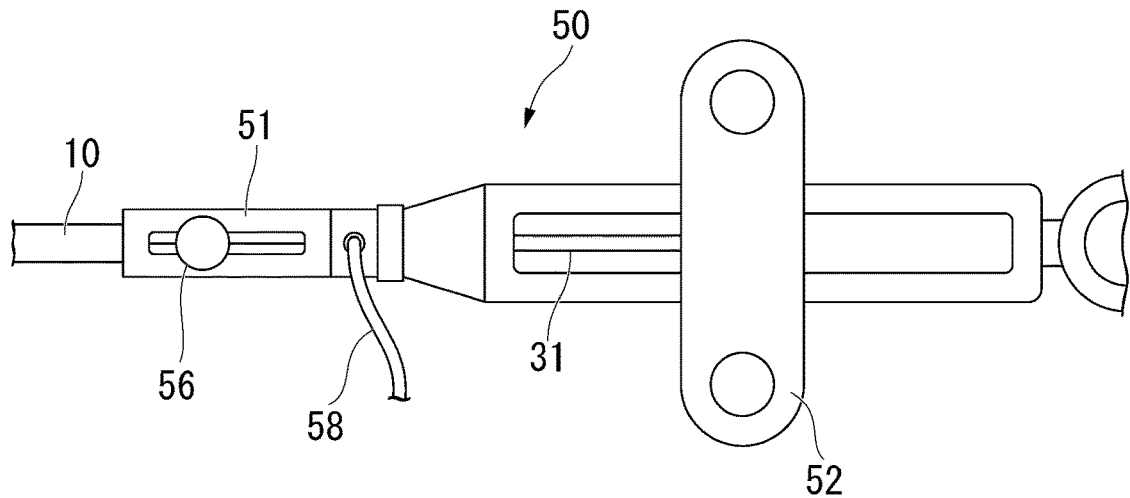
FIG. 2 is an enlarged view showing an operation portion of the endoscopic treatment device.

FIG. 2 is an enlarge view of the operation portion 50 viewed from a different direction from that of FIG. 1. As shown in FIG. 1 and FIG. 2, the operation portion 50 has an elongated main body 51, a main slider 52 attached to the main body 51, and two sub-sliders as the first sub-slider 55 and the second sub-slider 56.

The main body 51 is a member in a substantial tubular shape formed from resin and the like, and the main body 51 is connected to the proximal end portion of the sheath 10. The first wire 21, the second wire 31, the first insulative tube 25, and the second insulative tube 35 passing through the sheath 10 extend in the internal space of the main body 51.

The main slider 52 is attached to the main body 51 so as to be slidable with respect to the main body 51. The main slider 52 is connected to each proximal end portion of the parallelly extending first wire 21 and the second wire 31. Accordingly, by sliding the main slider 52 with respect to the main body 51, it is possible to advance/retract the first wire 21 and the second wire 31 with respect to the sheath 10.

Each of the first sub-slider 55 and the second sub-slider 56 is slidably attached to the main body 51 at a position closer to the sheath 10 than the movement range of the main slider 52. The proximal end portion of the first insulative tube 25 is connected to the first sub-slider 55. The proximal end portion of the second insulative tube 35 is connected to the second sub-slider 56.

When the first sub-slider 55 and the second sub-slider slide with respect to the main body 51, the first insulative tube 25 and the second insulative tube 35 advance/retract with respect to the sheath 10. The first insulative tube 25 and the second insulative tube 35 are independently operable with each other.

Figure 3:
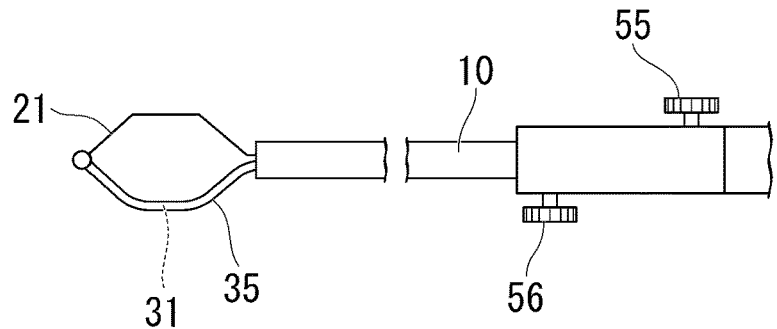
FIG. 3 is a view showing an embodiment of using the endoscopic treatment device.
Figure 4:
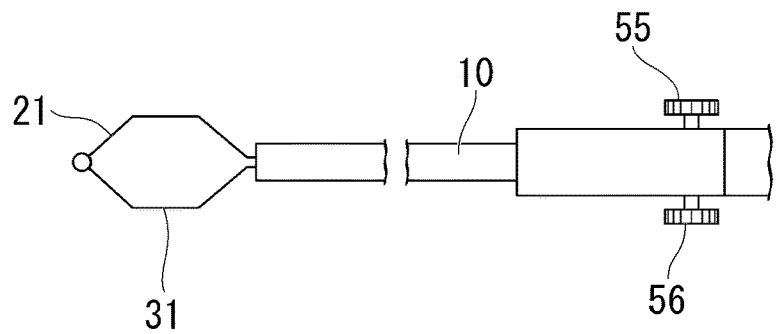
FIG. 4 is a view showing an embodiment of using the endoscopic treatment device.

Furthermore, in the state in which the first wire 21 and the second wire 31 protrude from the sheath 10, by operating the first sub-slider 55 and the second sub-slider 56, it is possible to advance/retract the first insulative tube 25 and the second insulative tube 35 with respect to the first wire 21 and the second wire 31. Accordingly, by operating each sub-slider 55, 56, it is possible to switch between a state, as shown in FIG. 3, in which the first wire 21 or the second wire 31 (shown as the second wire 31 in FIG. 3) protruded from the sheath 10 is insulation covered such that the tissue incision is impossible and a state, as shown in FIG. 4, in which the first wire 21 or the second wire 31 protruded from the sheath 10 is exposed to be able to perform the tissue incision.

The main body 51 is connected by a first wiring 57 configured to supply the high-frequency current to the first wire 21 and a second wiring 58 configured to supply the high-frequency current to the second wire 31. The first wiring 57 and the second wiring 58 are in contact with the first wire 21 and the second wire 31 so as to supply the current thereto in the internal space of the main body 51, respectively.

Next, the septum resection method according to the present embodiment using the endoscope 1 having the above-described configuration will be described.

The septum resection method according to the present embodiment can be performed to resect part of the septum exiting in the gastrointestinal tract with a predetermined width across a predetermined length. The septum resection method according to the present embodiment, for example, can be applied to remove part of the septum of the diverticulum formed in the gastrointestinal tract so as to make the ingesta difficult to be accommodated in the diverticulum. Hereinafter, the description will be made by taking the Zenker diverticulum as an example of one kind of the diverticulum generated in the esophagus.

Figure 5:
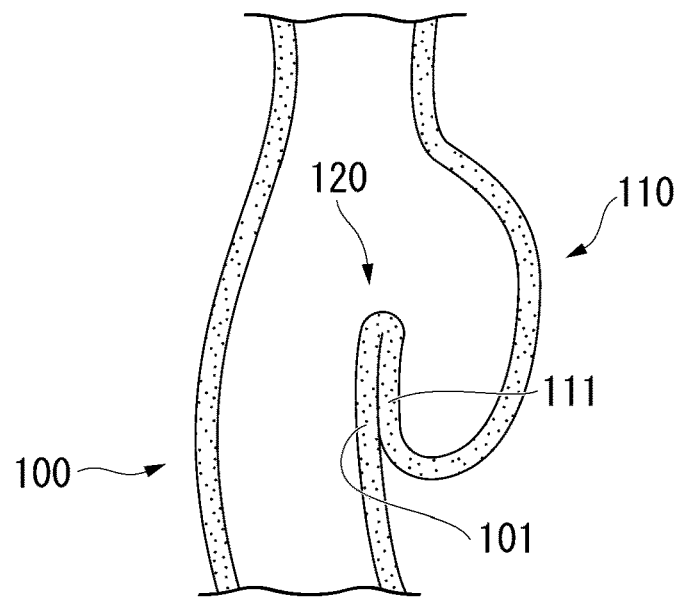
FIG. 5 is a schematic cross-sectional view of the Zenker diverticulum.

FIG. 5 is a schematic cross-sectional view of the Zenker diverticulum. With regard to the Zenker diverticulum, the bulging diverticulum 110 is hanging down. Part of the wall 111 of the hanging down diverticulum 110 comes in contact with part of the wall 101 of the healthy esophagus 100 and agglutinates therewith. Thus, the septum 120 is formed between the esophagus 100 and the diverticulum 110.

In the septum 120, since the esophagus wall and the diverticulum wall are agglutinated with each other, even the agglutinated part is cut, the esophagus will not communicate with the mediastinum and the thoracic cavity.

Figure 6:
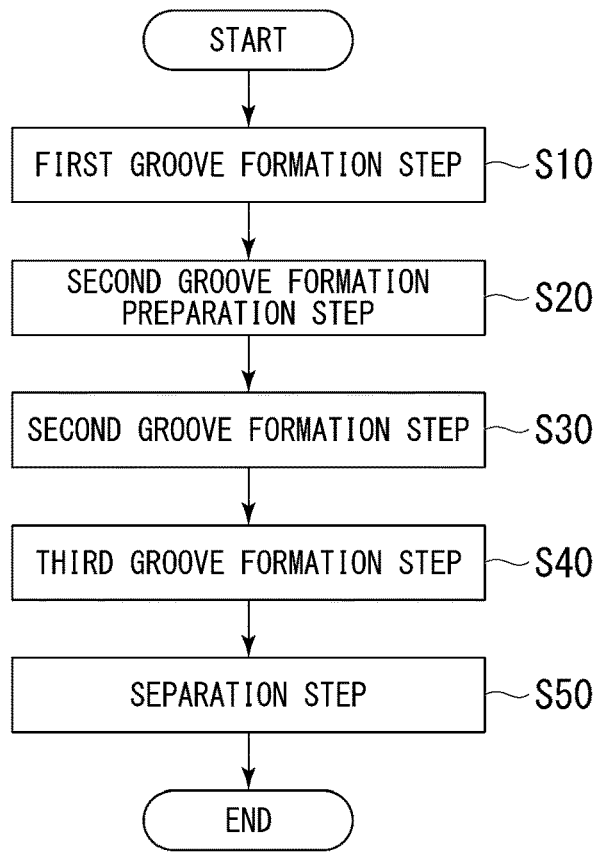
FIG. 6 is a flowchart showing procedures of a septum resection method according to the first embodiment of the present invention.

FIG. 6 is a flowchart showing the procedures of the septum resection method according to the present embodiment. The septum resection method has a first groove formation process S10, a second groove formation preparation process S20, a second groove formation process S30, a third groove formation process S40, and a dissection process S50.

In the first groove formation process S10, a first groove as a guide is formed in the septum by cutting the septum as the resection target in a straight-line shape.

In the situation of executing the septum resection method according to the present embodiment with respect to the septum 120, at first, the surgeon introduces the endoscope into the esophagus from the mouth of the patient to capture the opening of the diverticulum 110 in the field of view.

Figure 7:
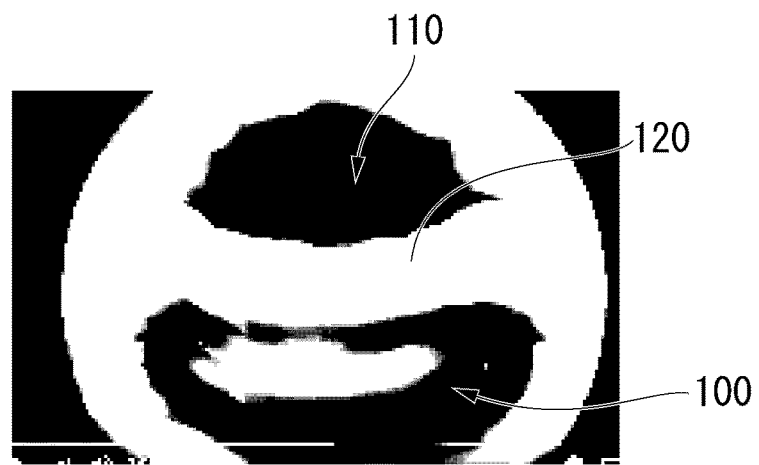
FIG. 7 is an endoscopic image capturing an entrance of the diverticulum in a field of view.

An endoscopic image capturing the opening of the diverticulum 110 in the field of view is shown in FIG. 7. The diverticulum 110 and the esophagus 100 are dived by the septum 120 formed therebetween, and the upper edge portion of the septum 120 is positioned near the opening of the diverticulum 110.

The surgeon inserts the treatment device 1 in the state in which the cutting portion 20 is almost accommodated in the sheath 10 into the channel of the endoscope, protrudes the sheath 10 from a distal end of the endoscope, and further protrudes the cutting portion 20 from the sheath 10. The treatment device 1 may be inserted in an external channel attached to the endoscope and protruded toward the distal end side of the endoscope.

Subsequently, the surgeon advances the second sub-slider 56 to cover the second wire 31 by the second insulative tube 35. Furthermore, the surgeon adjusts the orientation of the treatment device 1 so as to direct the exposed first wire 21 toward the septum 120.

A first state according to the present invention is defined as the state in which the second insulative tube 35 insulatively covers the second wire 31, and the first wire 21 is not covered by the first insulative tube 25 to be exposed.

Figure 8:
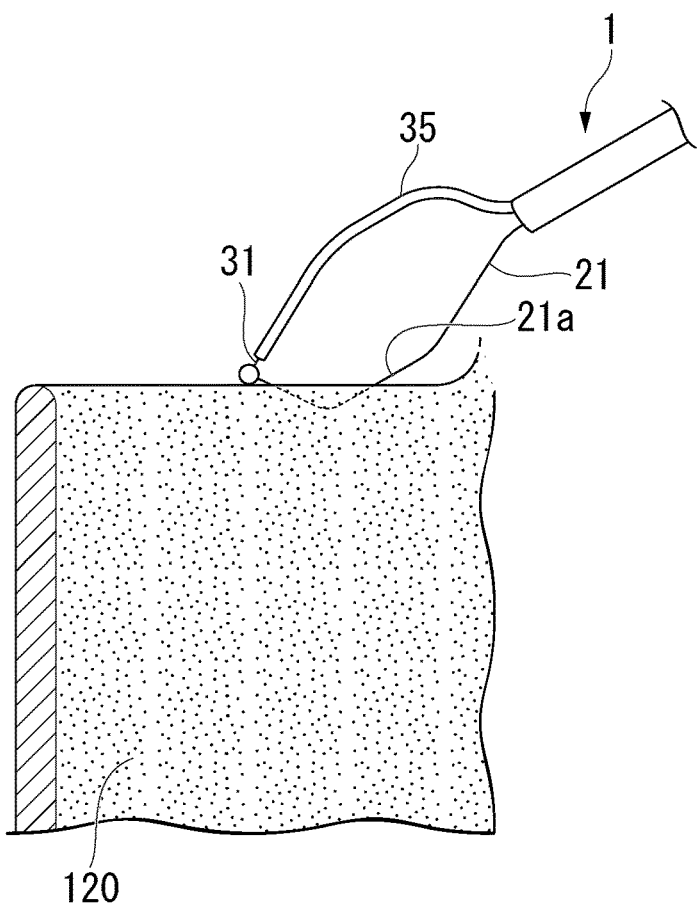
FIG. 8 is a view showing a first groove formation process of the septum resection method according to the first embodiment of the present invention.
Figure 9:
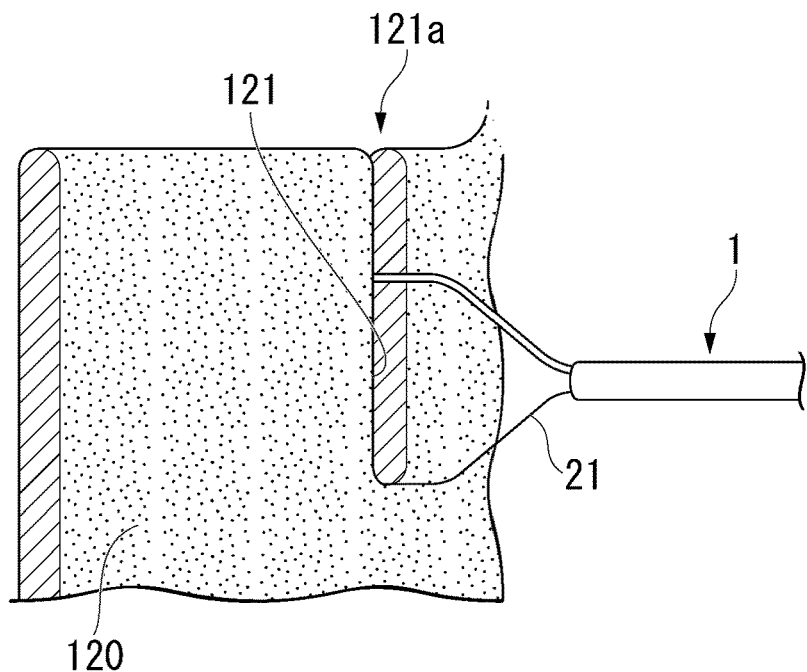
FIG. 9 is a view showing a state at the end of the first groove formation process.

As shown in FIG. 8, the surgeon causes the first wire 21 to come in contact with the upper edge portion of the septum 120 and forms an opening end by incising the edge portion. Furthermore, the surgeon proceeds to cut the septum 120 toward the stomach side along the traveling of the esophagus 100. At this time, it is possible to perform the stable incision by using the parallel portion 21a. When the first wire 21 has performed the incision by a predetermined length, as shown in FIG. 9, a first groove 121 which penetrates the septum 120 in the width direction and extends from the opening end 121a formed on the septum 120 is formed on the septum 120.

Therefore, the first groove formation process S10 is finished.

In the second groove formation preparation process S20, the surgeon advances the first sub-slider 55 to cover the first wire 21 with the first insulative tube 25 and moves the first wire 21 until the opening end 121a.

Figure 10:
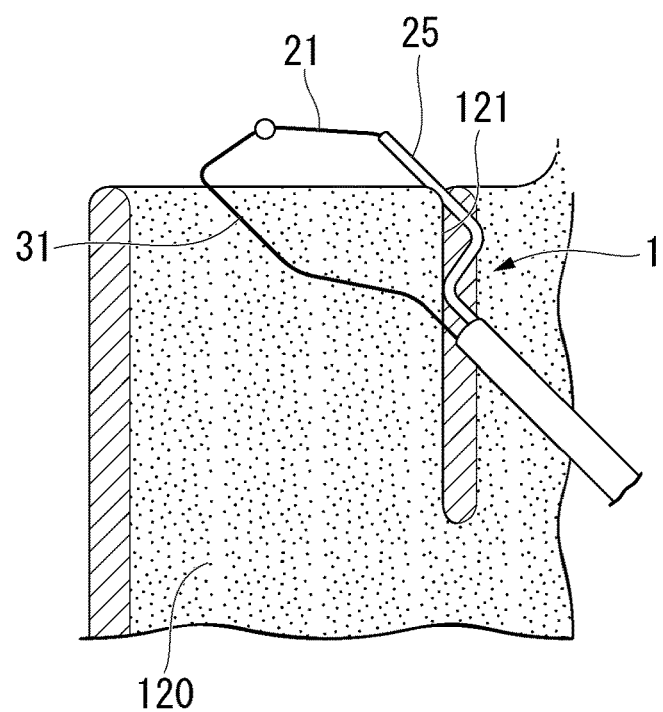
FIG. 10 is a view showing a second groove formation preparation process of the septum resection method.

At this time, as shown in FIG. 10, the surgeon may cause the second wire 31 to come in contact with the upper end of the septum 120 while keeping the position of the wire 21.

Figure 11:
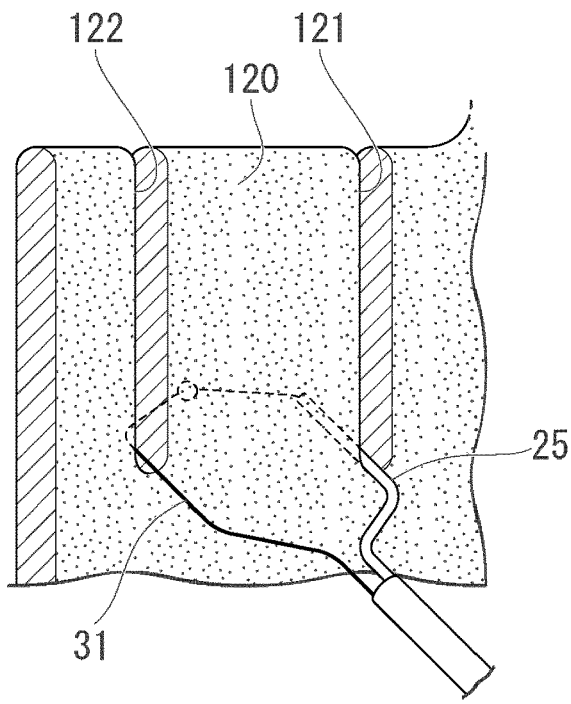
FIG. 11 is a view showing a second groove formation process of the septum resection method.

During the second groove formation preparation process S30, the surgeon retracts the second sub-slider to cause the second wire 31 to be exposed while keeping the positions of the first wire 21 and the second wire 31. The surgeon moves the first wire 21 which is insulatively covered by the first insulative tube 25 along the first groove 121, and continues to cut the septum 120 with the second wire 31. Therefore, as shown in FIG. 11, the second groove 122 is formed on the septum 120 that the second groove 122 penetrates the septum 120 in the width direction from the upper end of the septum 120 and the second groove 122 extends to be substantially parallel with the first groove 121 (hereinafter, the situation that the second groove 122 is parallel with the first groove 121 is included therein).

A second state according to the present invention is defined as the state in which the first insulative tube 25 insulatively covers the first wire 21, and the second wire 31 is not insulatively covered by the second insulative tube 35 to be exposed.

In the situation of incising the septum 120 using only one cutting member such as the wire and the like, high degree of skill is required to control the groove formed by the incision to extend in the desired direction. However, in the second groove formation process S30 in the septum resection method according to the present embodiment, since the relationship between the second wire 31 configured for the incision and the first wire 21 is maintained since the first wire 21 moves along the first groove 121, the second wire 31 is configured to cut the septum 120 while keeping a constant distance to the first groove 121. As a result, high degree of skill is not required to form the second groove 122 which extends to be substantially parallel to the first groove 121.

In the second groove formation process S30, the first wire 21 is covered by the first insulative tube 25 such that the first wire 21 will not cut the tissues of the septum so as to slip out from the first groove. Therefore, it is easy to form the second groove 122.

Figure 12:
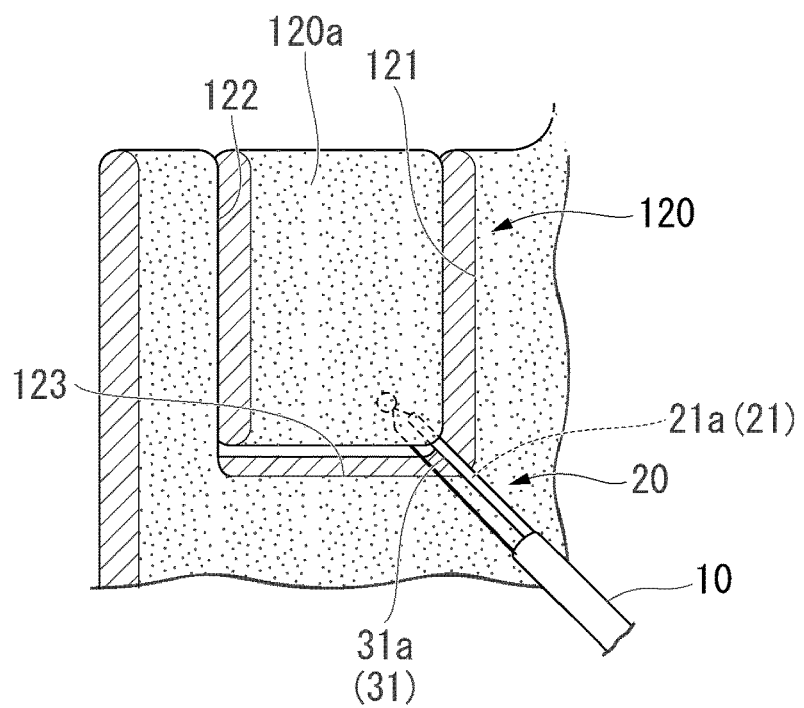
FIG. 12 is a view showing a third groove formation process of the septum resection method.

Subsequently, in the third groove formation process S40, the surgeon retracts the main slider 52. Due to the operation, the cutting portion 20 is gradually accommodated in the sheath 10 such that the parallel portion 31a of the second wire 31 and the parallel portion 21a of the first wire 21 approach to each other. Following this operation, the septum 120 is incised by the second wire 31 in the direction substantially vertical to the second groove 122. As shown in FIG. 12, a third groove 123 which penetrates the septum 120 in the width direction and connect s the first groove 121 and the second groove 122 is formed.

Subsequently, in the dissection process S50, a partial portion 120a of the septum 120 which is surrounded by the first groove 121, the second groove 122, and the third groove 123 is cut from the remaining portion so as to be removed.

As shown above, the septum dissection method according to the present embodiment is finished. The surgeon can collect the partial portion 120a as required and withdraw the treatment device 1 and the endoscope to finish the procedures of the surgery.

In the third groove formation method S40, besides the second wire 31, the first wire 31 may be also exposed to form the third groove 123 from both of the first groove 121 and the second groove 122.

Furthermore, the third groove 123 only has to be formed to connect the first groove 121 and the second groove 122, and the third groove 123 may not formed by connecting the terminal end portions of the first groove 121 and the second groove 122. However, it is preferable to form the third groove 123 by connecting the terminal end portions thereof since the removed region becomes substantially a rectangle shape to be able to maximize the removed region.

In the septum resection method according to the present embodiment, the region between the first groove 121 and the second groove 122 in the septum 120 as the resection target, which is formed in a belt shape having a width defined by the distance between the first groove 121 and the second groove 122, is removed. Therefore, in the septum after the resection, the first groove 121 and the second groove 122 as the stump portions are greatly apart from each other such that the agglutination of the stump portions is difficult to occur. As a result, in the situation of performing the septum resection method according to the present embodiment as the treatment to the Zenker diverticulum, it is possible to remove the septum for a larger area than the conventional method so as to significantly facilitate the discharge of the contents in the diverticulum while suitably suppressing the recurrence due to the agglutination and the like.

Also, in the second groove formation preparation process S20, both the first wire 21 entering the first groove 121 and the second wire 31 forming the new second groove 122 are adjusted to be positioned near the edge portion of the septum. Therefore, it is possible to execute the continuing second groove formation process S30 while keeping the distance between the first wire 21 and the septum edge portion and the distance between the second wire 31 and the septum edge portion to be substantially the same with each other. As a result, it is possible to suitably prevent the situation in which the second wire 31 moves following a circular arc shape with the first wire 21 as the center such that the second groove 122 is not substantially parallel to the first groove 121.

In the septum resection method according to the present method, in the second groove formation process S30, the second wire 31 being insulation covered may be moved along the first groove 121 and the second groove 122 may be formed by the exposed first wire 21.

On the other hand, according to the endoscopic treatment device 1 according to the present embodiment, all of the process of the septum resection method according to the present embodiment can be performed by a single device. Accordingly, it is not necessary to exchange devices during the execution of the septum resection method such that the septum resection can be efficiently performed.

Also, since the first wire 21 and the second wire 31 are inserted through the first insulative tube 25 and the second insulative tube 35 and are configured to be switchable between the insulatively covered state and the exposed state respectively, each process of the above-described septum resection method can be conveniently performed while suitably switching between the insulatively covered state and the exposed state. Furthermore, comparing to the embodiment of switching the first wire 21 and the second wire 31 between the resection-able state and the resection-unable state only by controlling the current supply to the wires, it is easy for the surgeon to recognize the resection-able state and the resection-unable state of each wire so as to be able to prevent the misrecognition by the surgeon.

Furthermore, since the insulative tip 23 is attached to the distal end of the cutting portion 20, even the distal end of the cutting portion 20 unintentionally comes in contact with the tissues and the like during the treatment, the distal end of the cutting portion 20 will not cauterize the tissues in contact therewith.

It is possible to apply various modifications to the treatment device 1 according to the present embodiment.

In the description above, it is described that the first wire and the second wire are configured to receive the currently supply via different wirings; however, instead of this solution, the wire receiving the current supply may be configured to be switchable so as to provide a single wiring only for the current supply.

Figure 13:
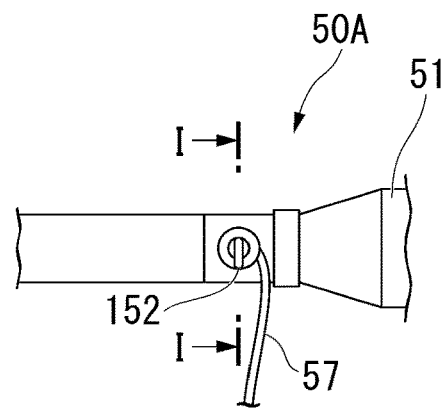
FIG. 13 is a view showing an operation portion in a modification example of the endoscope.

FIG. 13 is a view showing an example of the configuration in which the wire being supplied with the current is switchable.

In the operation portion 50A shown in FIG. 13, the first wiring 57 is connected to a switch 152 configured in the main body 51 for switching the supply target of the high-frequency current. The second wiring is not connected to the operation portion 50A.

Figure 14:
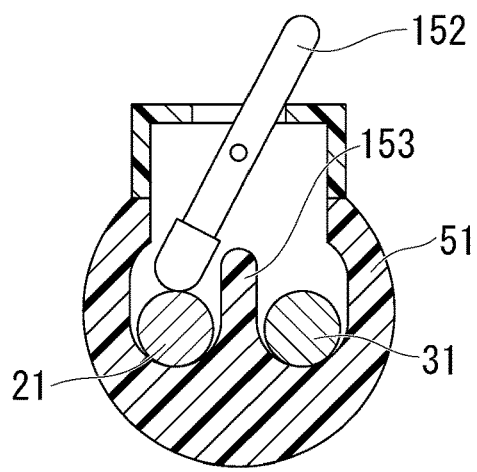
FIG. 14 is a cross-sectional view along the I-I line in FIG. 13.
Figure 15:
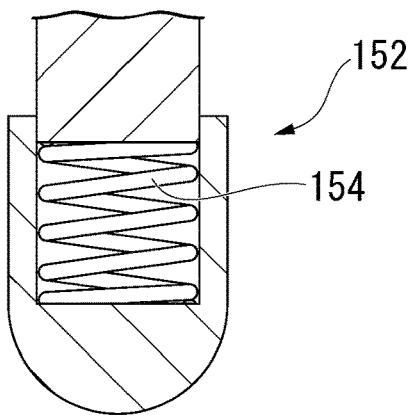
FIG. 15 is a cross-sectional view of a switch.

FIG. 14 is a cross-sectional view along the line I-I in FIG. 13. An insulative wall 153 is formed to extend in the longitudinal direction of the main body 51 so as to make the first wire 21 and the second wire 31 parallely extending in the main body 51 to be electrical insulative with each other. As shown in FIG. 15, the distal end portion of the switch 152 is provided with a spring 154, and the distal end portion of the switch 152 is configured to be switchable when the spring 154 is compressed. When the user applies a force to the switch 152, the spring 154 is compressed such that the distal end portion of the switch 152 moves backwardly so as to be able to overcome the wall 153. After overcoming the wall 153, the distal end portion of the switch 152 advances again to come in contact with the wire.

According to the above-described configuration, it is possible to switch the wire to which the current is supplied by appropriately operating the switch 152.

Furthermore, in the first wire 21 and the second wire 31, the regions between the tip 23 and the parallel portions, and the regions at the proximal end side of the parallel portions may be insulatively covered by coating and the like. According to the configuration, it is possible to more definitely prevent the unintentional cauterization with respect to the tissues.

Furthermore, the first wire 21 and the second wire 31 may be configured to be independently advanceable/retractable by connecting each proximal end portion of the first wire 21 and the second wire 31 to different slider respectively, while connecting the first wire 21 and the second wire 31 using the tip 23 and the like to maintain the relative relationship therebetween.

Another embodiment will be described referring to FIG. 16 to FIG. 22. In the following description, the common configurations which are already described will be designated with the same reference sings and the redundant description will be omitted.

Figure 16:
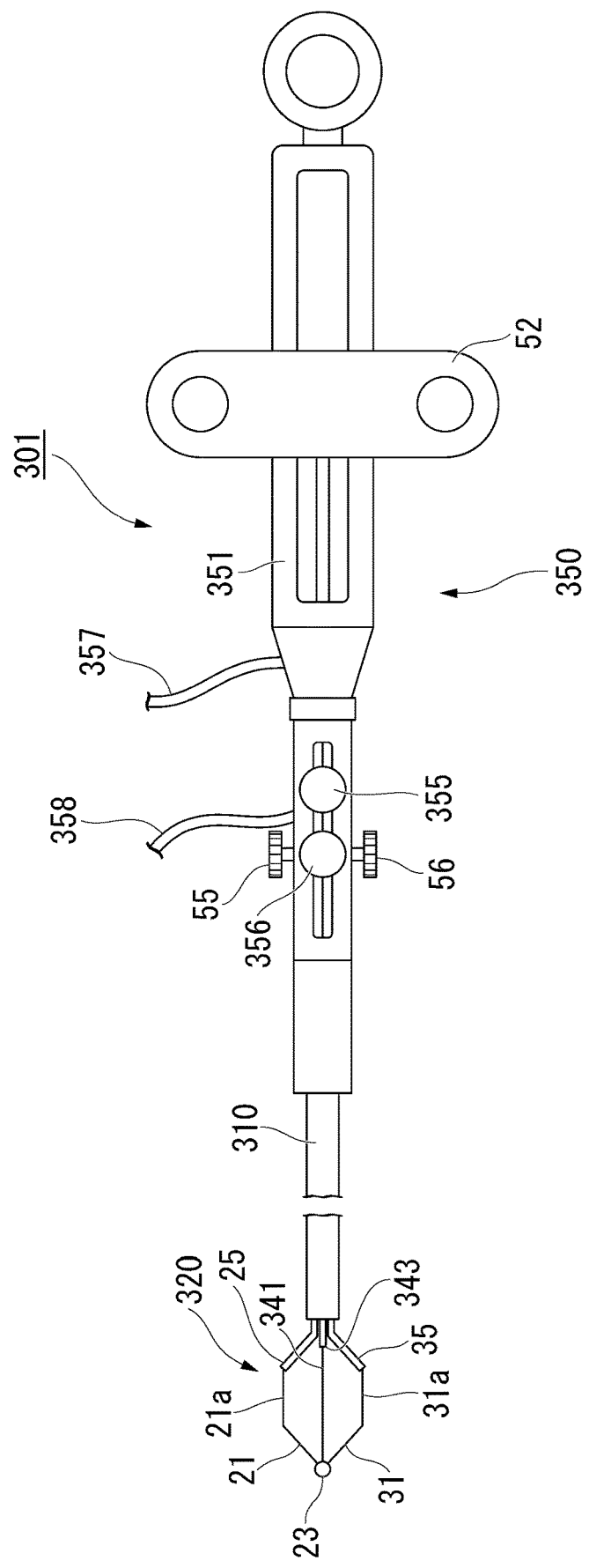
FIG. 16 is an overall view showing an endoscopic treatment device according to another exemplary embodiment of the present invention.

FIG. 16 is a view showing an overall configuration of an endoscopic treatment device 301. A cutting portion 320 of the treatment device 301 has a third wire 341 besides the first wire inserted through the first insulative tube 25 and the second wire 31 inserted through the second insulative tube 35.

Figure 17:
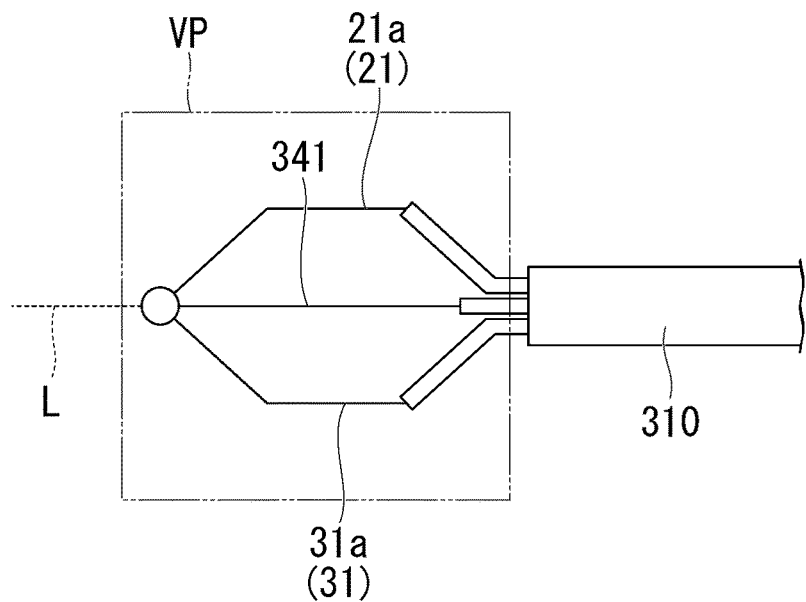
FIG. 17 is an enlarged view showing a distal end portion of the endoscopic treatment device.

FIG. 17 is an enlarged view showing the distal end portion of the endoscopic treatment device 301. FIG. 17 shows a state from a lateral-viewing of the endoscopic treatment device 301 which is made from a direction orthogonal to a virtual plane (plane) VP including the parallel portion 21a of the first wire 21 and the parallel portion 31a of the second wire 31 protruding from the sheath 310 and displaced. In FIG. 17, the third wire 341 protruding from the distal end of the sheath 310 is configured to extend between the first wire 21 and the second wire 31.

In FIG. 17, it is described that the third wire 341 extends along an extension line L of the central axis of the sheath 310, however, it is not an essential configuration of the present invention.

In the state shown in FIG. 17, the distance between the parallel portion 21a and the parallel portion 31a is the maximum value, however, it is not an essential configuration of the present invention.

The shape of the third wire 341 is not reformed such that the third wire 341 maintains the straight-line shape even protruding from the sheath 10. The sheath 310 is provided with three lumens, and the third wire 341 is disposed in a different lumen from that of the first wire 21 and the second wire 31 in a state of being inserted through the third insulative tube 343.

The third wire 341 may be reformed such that the third wire 341 protruding from the sheath 310 displaces in a different direction from that of the first wire 21 and the second wire 31. In this situation, when the third wire 341 protrudes from the sheath 310, it is possible to make the third wire 341 to displace outwardly with respect to the diameter direction of the sheath 310 and in a direction different from the displacement direction of the first wire 21 and the second wire 31.

In a cross-sectional surface of the sheath 310, a direct distance between each central axis of the three lumens of the sheath 310 and the central axis of the sheath 310 may be the same.

The distal end of each wire 21, 31, 341 is connected to the tip 23 such that each wire is configured to maintain the relationship with the other two wires. Each wire 21, 31, 341 is disposed in the different lumen of the sheath 310 so as to extend until the operation potion 350 in the sheath 310 without coming in contact with each other.

The basic configuration of the operation portion 350 is same with that according to the first embodiment. In the treatment device 310, the proximal end portions of the first wire 21 and the second wire 31 are joined together inside the main body 351 and then connected to the main slider 52. The main slider 52 is configured to be able to temporarily fixed with respect to the main body 351 by a conventional engaging mechanism such as a ratchet and the like not shown in the figure.

A second main slider 355 configured to advance/retract the third wire 341 is attached to the main body 351. The proximal end portion of the third wire 341 extending in the main body 351 is connected to the second main slider 355 such that the third wire 341 can be advanced/retracted with respect to the sheath 310 by sliding the second main slider 355 with respect to the main body 351. Also, when the second main slider 355 is slided while the main slider 52 is in the state of being fixed with respect to the main body 351, the third wire 341 can be advanced/retracted by maintaining the protrusion amount of the first wire 21 and the second wire 31 from the sheath 310.

The proximal portion of the third insulative tube 343 is connected to the sub-slider 356 attached to the main body 351. When the sub-slider 356 is advanced, the third wire 341 protruding from the sheath 310 can be insulatively covered.

A first wiring 357 configured to supply the high-frequency current to the first wire 21 and the second wire 31 and a second wiring 358 configured to supply the high-frequency current to the third wire 341 is connected to the main body 351.

Next, a septum resection method using the treatment device 301 according to the present embodiment will be described. The septum resection method according to the present embodiment is different from the septum resection method according to the first embodiment in that two second grooves are formed to sandwich the first groove in the second groove formation process.

Figure 18:
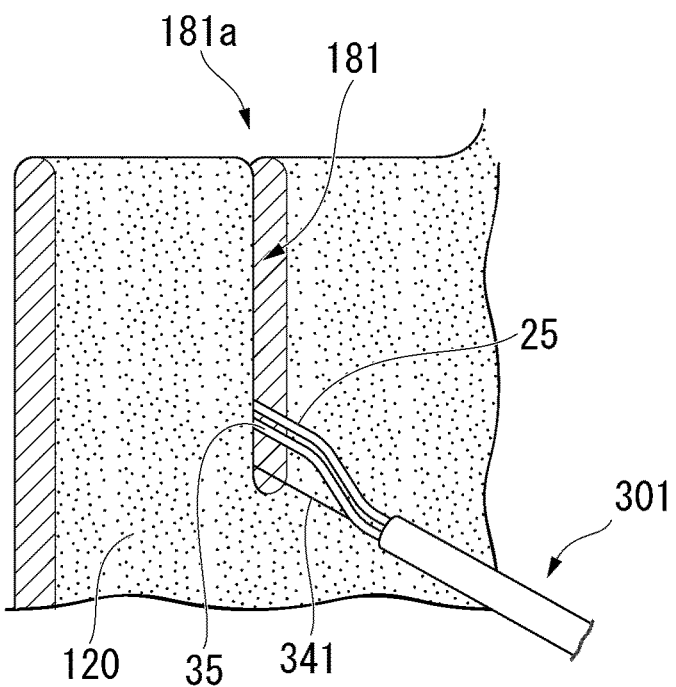
FIG. 18 is a view showing a first groove formation process in a septum resection method according to an exemplary embodiment.

In the first groove formation process S10, the surgeon supplies the current to the exposed third wire 341 to incise the septum 120 in the state in which the first wire 21 and the second wire 31 are covered by the first insulative tube 25 and the second insulative tube 35 respectively. Due to the operation, as shown in FIG. 18, a first groove 181 extending from the opening end 181a is formed. At this time, it is preferable to retract the first wire 21 and the second wire 31 with a predetermined amount and make the first wire 21 and the second wire 31 to approach the third wire 341 so as to prevent the first wire 21 and the second wire 31 from disturbing the first groove by the third wire 341. The first groove 181 according to the present embodiment is formed in the vicinity of the center in the width direction of the septum 120 in consideration of the following second groove formation process.

Subsequently, the surgeon executes the second groove formation preparation process S20 to operate the sub-slider 356 so as to cover the third wire 341 by the third insulative tube 343.

Figure 19:
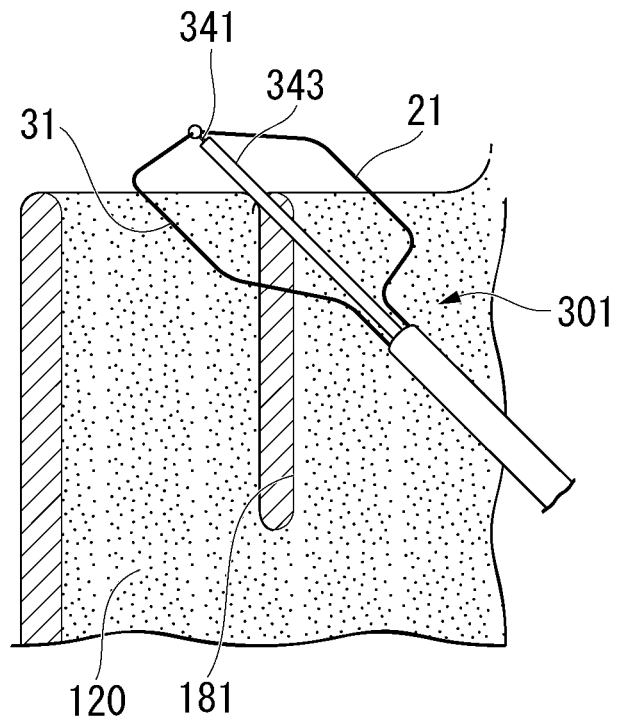
FIG. 19 is a view showing a second groove formation preparation process of the septum resection method.
Figure 20:
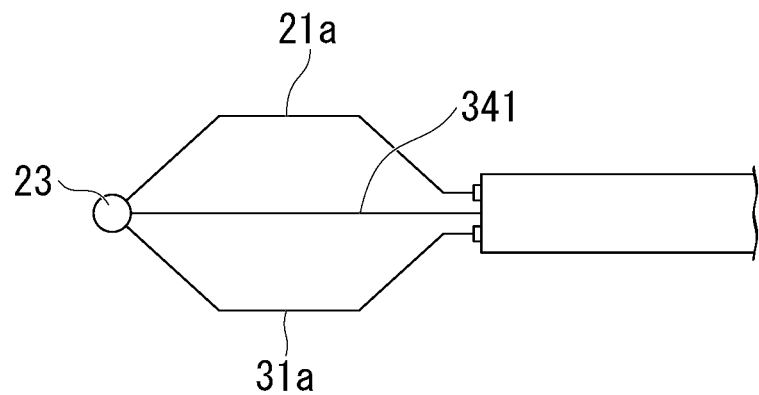
FIG. 20 is a view showing an embodiment of using the endoscopic treatment device.

At this time, as shown in FIG. 19, the surgeon may move the third wire 341 to be near the entrance of the first groove 181 and make the first wire 21 and the second wire 31 to be at the upper edge portion of the septum 120.

Figure 21:
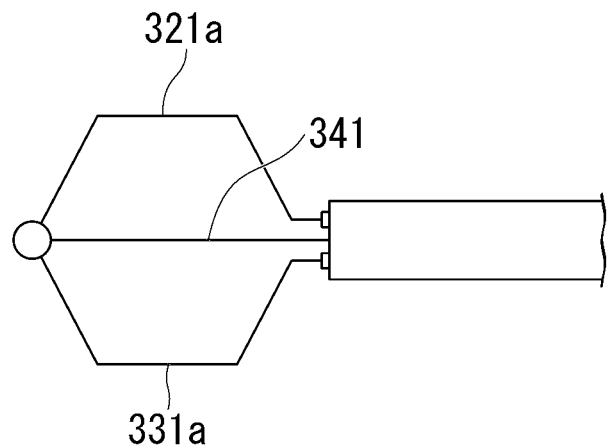
FIG. 21 is a view showing an embodiment of using the endoscopic treatment device.

In the second groove formation preparation process S20, the surgeon can adjust the distance between the third wire 341 and each parallel portion 21a, 31a by advancing/retracting the second main slider 355 in the state in which the main slider 52 is fixed to the main body 351. For example, when the surgeon retracts the second main slider 355 from the state shown in FIG. 20, the distance between the third wire 341 and each parallel portion 21a, 31a becomes larger as shown in FIG. 21. Accordingly, the surgeon can adjust the position where the second groove is formed in the continuing second groove formation process by operating the second main slider 355.

Figure 22:
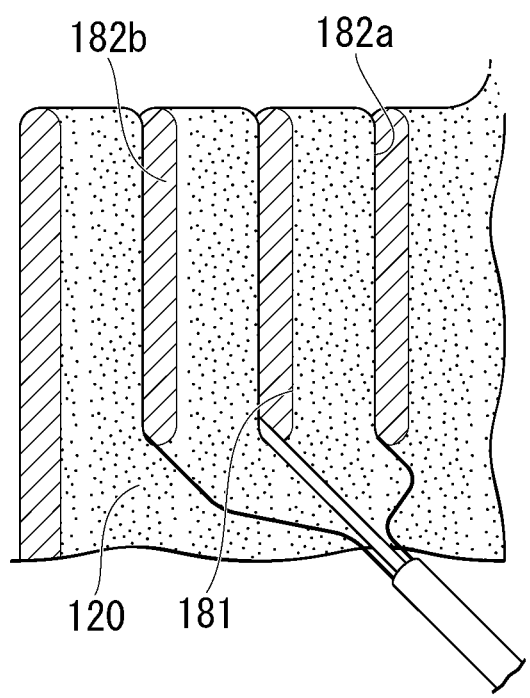
FIG. 22 is a view showing a second groove formation process of the septum resection method.

The surgeon executes the second groove formation process S30 after adjusting the distance between the third wire 341 and each parallel portion 21a, 31a as necessary. In the second groove formation process S30, the exposed first wire 21 being able to perform the incision forms the first groove 182a and the exposed second wire 31 being able to perform the incision forms the second groove 182b. As a result, as shown in FIG. 22, two second grooves 182a, 182b substantially parallel to the first groove 181 are simultaneously formed at two sides of the first groove 181.

A third state according to the present invention is defined as the state in which the third insulative tube 343 insulatively covers the third wire 341, and the first wire 21 and the second wire 31 are not covered by the insulative tubes so as to exposed.

Figure 23:
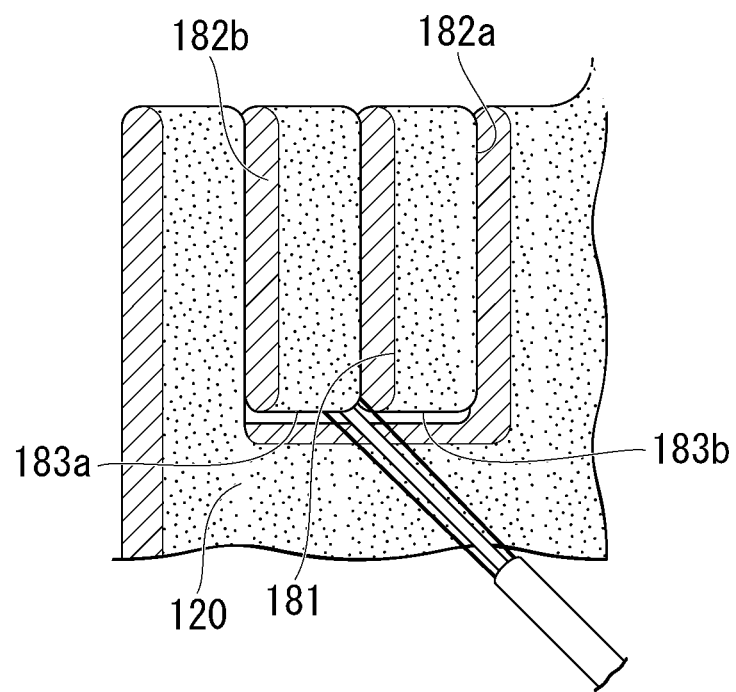
FIG. 23 is a view showing a third groove formation process of the septum resection method.

Subsequently, in the third groove formation process S40, when the surgeon retracts the main slider 52, as shown in FIG. 23, the parallel portions 21a, 31a incise the septum 120 while approaching the third wire 341. As a result, two third grooves including the third groove 183a connecting the second groove 182a and the first groove 181 and the third groove 183b connecting the second groove 182b and the first groove 181 are formed.

Thereafter, in the dissection process S50, a partial region of the septum 120 surrounded by the first groove 181, the second grooves 182a, 182b, and the third grooves 183a, 183b is cut off from the septum 120.

According to the endoscopic treatment device 301 according to the present embodiment, similar to the treatment device 1 according to the first embodiment, all of the process of the septum resection method according to the present embodiment can be performed by a single device such that the septum resection can be efficiently performed.

Also, the treatment device 301 is configured to make the third wire 341 to be advanceable/retractable while keeping the first wire and the second wire. In other words, the third wire 341 is configured to be relatively movable with respect to the first wire 21 and the second wire 31. As a result, as described above, it is easy to adjust the position for forming the second groove by adjusting the distance between the third wire 341 and the first wire 21 or the second wire 31.

Furthermore, two second grooves are simultaneously formed at the two sides of the third wire moving in the first groove, the situation in which the first wire and the second wire move following a circular arc shape with the third wire as the center does not occur. As a result, the second groove can be stably formed.

In the treatment device 301 according to the present embodiment, similar to the above-described modification examples, it is possible to us one single wiring for the current supply and a switch for switching to adopt a configuration such that the wire receiving the current supply is switchable.

The treatment device according to the present embodiment may be configured to have two main sliders to connect the first wire and the second wire with different main slider.

In the septum resection method according to the present embodiment, the wire configured to form the first groove may be any of the first wire to the third wire. Also, the relationship between the first groove and the two second grooves is not particularly limited thereto.

The embodiments of the invention have been described above with reference to the drawings, but specific structures of the invention are not limited to the embodiments and may include various modifications without departing from the scope of the invention.

For example, in each above-described embodiment, the example of the sheath having multiple lumens is described. However, instead of this configuration, a sheath having a single lumen may be configured by insulatively covering regions of a plurality of wires which are not used for the incision by suitable tubes or coating method.

The septum resection method according to the present invention is not limited to be performed to the above-described Zenker diverticulum and can be applied in various aspects. In other words, the septum resection method according to the present invention can be widely applied to the aspect in which part of the septum is desired to be cut off for a large area.

For example, the septum resection method according to the present invention can be applied to the treatment for enlarging the fistula connecting the bile duct and the duodenum. The general method of enlarging the fistula is known as disposing a balloon in the formed fistula and expanding the balloon; however, in many cases, the effect of such a method is known to be temporary. According to the septum resection method according to the present invention, by resecting a partial region of the septum by a predetermined width from the opening edge portion of the fistula, it is difficult for the enlarged fistula to shrink again.

Also, in the situation of forming the fistula connecting the stomach and the pancreas in the necrosectomy with respect to the pancreas, the septum resection method according to the present invention can be applied. If the stomach wall is cut off to enlarge the fistula connecting the stomach and the pancreas, the volume of the tissues removed at once is increased so as to significantly reduce the necessary time of the procedures.

The septum resection method according to the present invention can be applied by using a single conventional endoscopic treatment device or a combination of the conventional endoscopic treatment devices. In other words, the septum resection method according to the present invention is not limited to the embodiments using the endoscopic treatment device according to the present invention.

The embodiments of the invention have been described above with reference to the drawings, but specific structures of the invention are not limited to the embodiments and may include various modifications without departing from the scope of the invention. The invention is not limited to the above-mentioned embodiments and is limited only by the accompanying claims.

What is claimed is:

1. A septum resection method performed using an endoscopic treatment device to resect part of a septum in a gastrointestinal organ, comprising:
    forming a first groove in the septum by forming an opening end by cutting an edge portion of the septum using a first wire of the endoscopic treatment device, the first groove extending from the opening end;
    after forming the first groove, forming a second groove in the septum substantially parallel to the first groove by using a second wire of the endoscopic treatment device and cutting the edge portion of the septum with the second wire while moving the first wire being insulatively covered by a first insulative tube of the endoscopic treatment device along the first groove;
    forming a third groove by cutting the septum to connect the first groove and the second groove after forming the second groove; and
    removing part of the septum surrounded by the first groove, the second groove, and the third groove from the gastrointestinal organ, wherein the endoscopic treatment device includes:
        a sheath having a distal end portion and a proximal end portion,
        the first wire inserted through the sheath, the first wire being configured to protrude from the distal end portion of the sheath,
        the second wire inserted through the sheath, the second wire being configured to protrude from the distal end portion of the sheath, and
        the first insulative tube configured to cover the first wire protruding from the sheath, the first insulative tube being configured to move with respect to the first wire.

2. The septum resection method according to claim 1, further comprising moving the first wire to the opening end after forming the first groove and before forming the second groove.

3. The septum resection method according to claim 1, wherein the endoscopic treatment device further includes:
    an insulative member configured to connect distal ends of the first wire and the second wire;
    a second insulative tube configured to cover the second wire protruding from the sheath, the second insulative tube being configured to move with respect to the second wire, wherein:
        the endoscopic treatment device is configured to switch between a first state in which the second wire protruding from the sheath is covered by the second insulative tube and a second state in which the first wire protruding from the sheath is covered by the first insulative tube.

4. A septum resection method for resecting part of a septum in a gastrointestinal organ by using an endoscopic treatment device comprising:
    forming a first groove in the septum using one of a first wire, a second wire, or a third wire of the endoscopic treatment device;
    forming a pair of second grooves in the septum substantially parallel to the first groove after forming the first groove;
    forming a third groove by cutting the septum to connect the first groove and the pair of second grooves; and
    removing part of the septum surrounded by the first groove, the pair of second grooves, and the third groove from the gastrointestinal organ, wherein the endoscopic treatment device includes:
        a sheath having a distal end portion and a proximal end portion, the first wire inserted through the sheath, the first wire being configured to protrude from the distal end portion of the sheath,
        the second wire inserted through the sheath, the second wire being configured to protrude from the distal end portion of the sheath, and
        the third wire protruding from the distal end portion of the sheath between the first wire and the second wire.

5. The septum resection method according to claim 4, further comprising:
    forming an opening end by cutting an edge portion of the septum using one of the first wire, the second wire, or the third wire, the first groove extending from the opening end, and
    forming one groove of the pair of second grooves by using the first wire and forming the other groove of the pair of second grooves by using the second wire while moving the third wire being insulatively covered by an insulative tube along the first groove after cutting the edge portion of the septum by the first wire and the second wire.

6. The septum resection method according to claim 5, further comprising moving the third wire to the opening end, after forming the first groove and before forming the pair of second grooves.

7. The septum resection method according to claim 4, wherein the endoscopic treatment device further includes:
    a first insulative member configured to connect distal ends of the first wire and the second wire, the first insulative member is connected to the distal end of the first wire, the distal end of the second wire, and a distal end of the third wire;
    a second insulative member configured to cover the second wire protruding from the sheath, the second insulative member being configured to move with respect to the second wire, a third insulative member being movable with respect to the third wire, the third wire being inserted through the third insulative member such that the third insulative member covers the third wire protruding from the sheath, wherein the endoscopic treatment device is configured to:

switch between a first state in which the second wire protruding from the sheath is covered by the second insulative member and a second state in which the first wire protruding from the sheath is covered by the first insulative member; and switch among the first state, the second state, and a third state in which the third wire protruding from the sheath is covered by the third insulative member.

* * * * *